(12) United States Patent
Matsushita et al.

(10) Patent No.: US 9,132,048 B2
(45) Date of Patent: Sep. 15, 2015

(54) WATER-ABSORBENT SHEET STRUCTURE

(75) Inventors: Hideki Matsushita, Himeji (JP);
Haruka Inaba, Maizuru (JP); Kana Kudo, Himeji (JP); Junichi Takatori, Himeji (JP)

(73) Assignee: SUMITOMO SEIKA CHEMICALS CO., LTD., Kako-gun (JP)

( * ) Notice: Subject to any disclaimer, the term of this patent is extended or adjusted under 35 U.S.C. 154(b) by 136 days.

(21) Appl. No.: 13/819,591

(22) PCT Filed: Sep. 27, 2011

(86) PCT No.: PCT/JP2011/072044
§ 371 (c)(1),
(2), (4) Date: Feb. 27, 2013

(87) PCT Pub. No.: WO2012/043546
PCT Pub. Date: Apr. 5, 2012

(65) Prior Publication Data
US 2013/0178814 A1 Jul. 11, 2013

(30) Foreign Application Priority Data

Sep. 28, 2010 (JP) ................ 2010-217653

(51) Int. Cl.
*A61F 13/15* (2006.01)
*A61F 13/53* (2006.01)
*A61F 13/49* (2006.01)
*A61F 13/47* (2006.01)
*A61F 13/536* (2006.01)
*A61F 13/475* (2006.01)
*A61F 13/533* (2006.01)
*A61F 13/537* (2006.01)

(52) U.S. Cl.
CPC ........... *A61F 13/53* (2013.01); *A61F 13/15707* (2013.01); *A61F 13/4704* (2013.01); *A61F13/4756* (2013.01); *A61F 13/49001* (2013.01); *A61F 13/533* (2013.01); *A61F 13/536* (2013.01); *A61F 2013/53778* (2013.01); *Y10T 428/24488* (2015.01)

(58) Field of Classification Search
CPC ............ A61F 13/4704; A61F 13/4756; A61F 13/49001; A61F 13/536; A61F 2013/530868; A61F 2013/530875; A61F 2013/530883; A61F 2013/530897; A61F 2013/5315; A61F 2013/5349; A61F 2013/53739; A61F 2013/53778
USPC .................................. 604/379, 380, 385.101
See application file for complete search history.

(56) References Cited

U.S. PATENT DOCUMENTS

| | | | |
|---|---|---|---|
| 3,881,490 A | 5/1975 | Whitehead et al. | |
| 4,079,739 A | 3/1978 | Whitehead | |
| 5,833,679 A | 11/1998 | Wada | |
| 5,994,614 A | 11/1999 | Wada et al. | |
| 6,440,113 B1 * | 8/2002 | Brisebois et al. | 604/385.01 |
| 6,874,892 B1 * | 4/2005 | McDaniel | 353/84 |
| 6,914,018 B1 | 7/2005 | Uitenbroek et al. | |
| 6,953,451 B2 * | 10/2005 | Berba et al. | 604/385.01 |
| 6,964,655 B2 * | 11/2005 | Killeen et al. | 604/385.04 |
| 7,626,072 B2 | 12/2009 | Mocadlo | |
| 7,754,940 B2 | 7/2010 | Brisebois et al. | |
| 7,942,858 B2 * | 5/2011 | Francoeur et al. | 604/385.101 |
| 2002/0029024 A1 | 3/2002 | Furuya et al. | |
| 2003/0114809 A1 | 6/2003 | Gagliardi et al. | |
| 2004/0116884 A1 | 6/2004 | Fujii et al. | |
| 2004/0122386 A1 | 6/2004 | Mocadlo | |
| 2004/0254556 A1 | 12/2004 | Brisebois et al. | |
| 2007/0129699 A1 | 6/2007 | Ohtsuka et al. | |
| 2008/0281287 A1 * | 11/2008 | Marcelo et al. | 604/383 |
| 2008/0294140 A1 * | 11/2008 | Ecker et al. | 604/385.23 |
| 2011/0111199 A1 | 5/2011 | Takatori et al. | |
| 2011/0151228 A1 | 6/2011 | Takatori et al. | |
| 2011/0270204 A1 | 11/2011 | Fukudome et al. | |
| 2011/0276019 A1 | 11/2011 | Kakimoto et al. | |
| 2011/0288514 A1 * | 11/2011 | Kuroda et al. | 604/380 |
| 2012/0029456 A1 | 2/2012 | Takatori et al. | |
| 2012/0089108 A1 | 4/2012 | Ueda et al. | |
| 2012/0203191 A1 | 8/2012 | Maruo et al. | |
| 2012/0288701 A1 | 11/2012 | Matsushita et al. | |
| 2012/0308799 A1 | 12/2012 | Yamaguchi et al. | |
| 2012/0328861 A1 | 12/2012 | Hinayama et al. | |

| 2012/0328862 | A1 | 12/2012 | Fukudome et al. |
| 2013/0018349 | A1 | 1/2013 | Takatori et al. |
| 2013/0046263 | A1 | 2/2013 | Fukudome et al. |
| 2013/0338621 | A1 | 12/2013 | Ecker et al. |

FOREIGN PATENT DOCUMENTS

| CN | 2680228 | Y | 2/2005 |
| CN | 1720069 | A | 1/2006 |
| CN | 1822806 | A | 8/2006 |
| CN | 201219950 | Y | 4/2009 |
| CN | 101677885 | A | 3/2010 |
| EP | 0 829 245 | A2 | 3/1998 |
| JP | 53-83396 | | 7/1978 |
| JP | 63-27406 | U | 2/1988 |
| JP | 09-253130 | A | 9/1997 |
| JP | 10-272155 | | 10/1998 |
| JP | 2000-225145 | | 8/2000 |
| JP | 2002-65738 | | 3/2002 |
| JP | 2004-520856 | | 7/2004 |
| JP | 2005-152241 | | 6/2005 |
| JP | 2007-117111 | A | 5/2007 |
| JP | 2007-175515 | A | 7/2007 |
| JP | 2008-279774 | | 11/2008 |
| JP | 2009-172127 | A | 8/2009 |
| WO | WO 2010/004894 | A1 | 1/2010 |

OTHER PUBLICATIONS

Extended European Search Report issued Apr. 16, 2014, in European Patent Application No. 11829099.8.
International Search Report issued Nov. 8, 2011 in PCT/JP2011/072044.
Combined Chinese Office Action and Search Report issued Mar. 24, 2014 in Patent Application No. 201180046895.7.
U.S. Appl. No. 14/369,580, filed Jun. 27, 2014, Matsushita, et al.

* cited by examiner

*Primary Examiner* — Lynne Anderson
(74) *Attorney, Agent, or Firm* — Oblon, McClelland, Maier & Neustadt, L.L.P.

(57) ABSTRACT

A water-absorbent sheet structure comprising a structure in which an absorbent layer containing a water-absorbent resin is sandwiched with a hydrophilic nonwoven fabric from an upper side and a lower side of the absorbent layer, characterized in that at least one side of the upper side and the lower side of the water-absorbent sheet structure is subjected to embossing, wherein a central region W1 of a water-absorbent sheet structure 1 along a longitudinal direction of the structure 1 is subjected to: wavy embossing 2 comprising one wavy embossing extending along the longitudinal direction, wherein the embossing comprises one or more discontinued segments of the embossing, and linear embossing 4 in a direction from each of tips 3 of wavy forms formed by the wavy embossing 2 towards an edge portion contouring along the longitudinal direction of the water-absorbent sheet structure 1, and wherein a branched structure of embossing formed by the wavy embossing 2 and the linear embossing 4 has an approximate Y-shape-form, and wherein the edge portion contouring along the longitudinal direction of the water-absorbent sheet structure 1 comprises non-embossing regions W2, W2' not subjected to embossing, extending along the longitudinal direction, and further wherein an area of the embossing provided on the water-absorbent sheet structure 1 is from 2 to 25% of an entire area of the water-absorbent sheet structure 1; and an absorbent article comprising the water-absorbent sheet structure, sandwiched between a liquid-permeable sheet and a liquid-impermeable sheet. According to the present invention, some effects are exhibited that a water-absorbent sheet structure which has a fast permeation rate of a liquid and is less likely to cause liquid leakage can be provided by subjecting at least an upper side or a lower side of the water-absorbent sheet structure to a specified emboss shape even when the water-absorbent sheet structure contains very little amount of pulps.

11 Claims, 10 Drawing Sheets

WATER-ABSORBENT SHEET STRUCTURE

TECHNICAL FIELD

The present invention relates to a thin water-absorbent sheet structure which can be used in the fields of hygienic materials and the like. More specifically, the present invention relates to a water-absorbent sheet structure containing a very small amount of pulp, which can be suitably used in absorbent articles, such as disposable diapers and incontinence pads, which has a fast permeation rate of a liquid and does not cause liquid leakage. Furthermore, the present invention relates to an absorbent article obtainable from the water-absorbent sheet structure.

BACKGROUND ART

Body liquid absorbent articles represented by disposable diapers or the like comprise an absorbent material for absorbing a liquid such as a body liquid, a flexible liquid-permeable surface sheet (top sheet) positioned on a side contacting a body, and a liquid-impermeable backside sheet (back sheet) positioned on a side opposite to that contacting the body.

Conventionally, there have been increasing demands for thinning and light-weighing of absorbent articles, from the viewpoint of designing property, convenience upon carrying, and efficiency upon distribution. Further, in the recent years, there have been growing needs for so-called eco-friendly intentions, in which resources are effectively utilized so that use of natural materials that require a long time to grow such as trees is avoided as much as possible, from the viewpoint of environmental protection.

In view of the above, as a water-absorbent sheet structure containing very small amount of crushed pulp fibers from wood, and having excellent fundamental properties, e.g. fast liquid permeation rate, sufficient liquid absorbent properties, small amount of liquid re-wet, small liquid leakage, shape retaining ability, and is capable of accomplishing thinning, a proposal has been made for a water-absorbent sheet structure having a structure in which a given amount of a water-absorbent resin and a given amount of a hot melt adhesive are sandwiched with two or more sheets of hydrophilic nonwoven fabrics having a given basis weight, e.g. see Patent Publication 1.

On the other hand, in the conventional absorbent material mentioned above, in order to improve the effects in absorption rate and fittability and prevention of deformation in shapes, a proposal has been made to subject the absorbent material to embossing, e.g. Patent Publication 2.

PRIOR ART PUBLICATIONS

Patent Publications

Patent Publication 1: International Publication WO 2010/004894 Pamphlet
Patent Publication 2: Japanese Patent Laid-Open No. Hei-10-272155

SUMMARY OF THE INVENTION

Problems to be Solved by the Invention

While the water-absorbent sheet structure disclosed in Patent Publication 1 has sufficiently excellent fundamental properties mentioned above, a proposal for a water-absorbent sheet structure which is even more excellent, especially in fast liquid permeation rate and small liquid leakage, has been desired.

It has been tried that the above-mentioned water-absorbent sheet structure is subjected to embossing disclosed in Patent Publication 2; however, expected improvements in fast liquid permeation rate, small liquid leakage and the like could not be found.

An object of the present invention is to provide a water-absorbent sheet structure having excellent liquid permeability and a small liquid leakage, and is capable of accomplishing thinning. A further object of the present invention is provide an absorbent article obtained from the water-absorbent sheet structure.

Means to Solve the Problems

Specifically, the gist of the present invention relates to:
[1] a water-absorbent sheet structure comprising a structure in which an absorbent layer containing a water-absorbent resin is sandwiched with a hydrophilic nonwoven fabric from an upper side and a lower side of the absorbent layer, characterized in that at least one side of the upper side and the lower side of the water-absorbent sheet structure is subjected to embossing, wherein a central region W1 of a water-absorbent sheet structure 1 along a longitudinal direction of the structure 1 is subjected to:

wavy embossing 2 comprising one wavy embossing extending along the longitudinal direction, wherein the embossing comprises one or more discontinued segments of the embossing, and linear embossing 4 in a direction from each of tips 3 of wavy forms formed by the wavy embossing 2 towards an edge portion contouring along the longitudinal direction of the water-absorbent sheet structure 1, and wherein a branched structure of the embossing formed by the wavy embossing 2 and the linear embossing 4 has an approximate Y-shape-form, and wherein the edge portion contouring along the longitudinal direction of the water-absorbent sheet structure 1 contains non-embossing regions W2, W2' not subjected to embossing, extending along the longitudinal direction, and further wherein an area of the embossing provided on the water-absorbent sheet structure 1 is from 2 to 25% of an entire area of the water-absorbent sheet structure 1; and

[2] an absorbent article comprising the water-absorbent sheet structure as defined in the above [1], sandwiched between a liquid-permeable sheet and a liquid-impermeable sheet.

Effects of the Invention

According to the present invention, some effects are exhibited that a water-absorbent sheet structure which has a fast permeation rate of a liquid and is less likely to cause liquid leakage can be provided by subjecting at least an upper side or a lower side of the water-absorbent sheet structure to a specified emboss shape even when the water-absorbent sheet structure contains very little amount of pulps. Therefore, an absorbent article having excellent absorption properties can be provided by incorporating the water-absorbent sheet structure into the absorbent article, such as disposable diapers, as an absorbent material.

MODES FOR CARRYING OUT THE INVENTION

Figure 1:
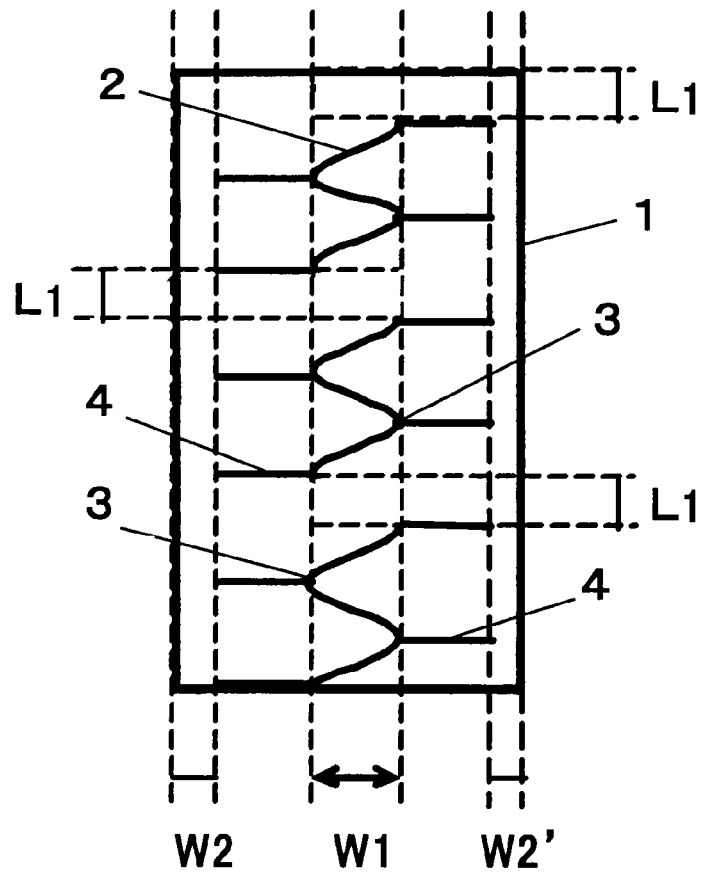
FIG. 1 The figure is a plan view schematically showing one example of a water-absorbent sheet structure of the present invention. In the water-absorbent sheet structure 1, a central region W1 of a water-absorbent sheet structure 1 along a longitudinal direction of the structure 1 is subjected to one wavy embossing 2 extending along the longitudinal direction. Here, the wavy embossing 2 comprises one or more discontinued segments (specifically three segments) of embossing. In the FIG. 1, L1 is a length of the discontinued segments of the embossing (distance between embossing). Further, the water-absorbent sheet structure 1 is subjected to linear embossing 4 in a direction from each tips 3 of wavy forms formed by the wavy embossing 2 towards an edge portion contouring along the longitudinal direction of the water-absorbent sheet structure 1. Further, the edge portion contouring along the longitudinal direction of the water-absorbent sheet structure 1 comprises non-embossing regions W2, W2' not provided with embossing, extending along the longitudinal direction. Moreover, a branched structure of embossing formed by the wavy embossing 2 and the linear embossing 4 has an approximate Y-shaped form.

The water-absorbent sheet structure according to the present invention is a water-absorbent sheet structure comprising a structure in which an absorbent layer containing a water-absorbent resin is sandwiched with hydrophilic nonwoven fabrics from an upper side and a lower side of the absorbent layer, wherein at least one side of the upper side and the lower side of the water-absorbent sheet structure is subjected to a specified emboss shape.

As the water-absorbent resins used in the present invention, known water-absorbent resins can be used. Examples of the water-absorbent resins include hydrolysates of starch-acrylonitrile graft copolymers, neutralized products of starch-acrylic acid graft polymers, saponified products of vinyl acetate-acrylic acid ester copolymers, crosslinked products of partially neutralized products of acrylic acid polymers, partially neutralized products of polyacrylic acid, and the like. Among these water-absorbent resins, the crosslinked products of partially neutralized products of acrylic acid polymers are preferred, from the industrial viewpoints such as supplying ability and costs. Methods for synthesizing crosslinked products of partially neutralized products of acrylic acid polymers include reversed phase suspension polymerization method and aqueous solution polymerization method. Among these polymerization methods, the water-absorbent resins obtained according to reversed phase suspension polymerization method are more preferably used, from the viewpoint of excellent flowability of the resulting particles, smaller amounts of fine powder, high water-absorbent properties, such as water-absorption capacity and water-absorption rate.

The water-absorbent resin is contained in the water-absorbent sheet structure according to the present invention in an amount of preferably from 100 to 1,000 g per one square-meter of the water-absorbent sheet structure, i.e. from 100 to 1,000 $g/m^2$, more preferably from 140 to 800 $g/m^2$, even more preferably from 180 to 700 $g/m^2$, and still even more preferably from 200 to 600 $g/m^2$, from the viewpoint of obtaining sufficient liquid absorbent properties even when the above-mentioned water-absorbent sheet structure is used for an absorbent article. It is preferable that the water-absorbent resin is contained in an amount of 100 $g/m^2$ or more, from the viewpoint of exhibiting sufficient liquid absorbent properties as a water-absorbent sheet structure, thereby suppressing re-wetting, and it is preferable that the water-absorbent resin is contained in an amount of 1,000 $g/m^2$ or less, from the viewpoint of suppressing the gel-blocking phenomenon of the water-absorbent resin from being caused, exhibiting liquid diffusibility as a water-absorbent sheet structure, and further improving a liquid permeation rate.

The hydrophilic nonwoven fabrics usable in the water-absorbent sheet structure according to the present invention are not particularly limited, as long as the hydrophilic nonwoven fabrics are known hydrophilic nonwoven fabrics in the field of art. The hydrophilic nonwoven fabrics include hydrophilic nonwoven fabrics made of polyolefin fibers such as polyethylene (PE) and polypropylene (PP); polyester fibers such as polyethylene terephthalate (PET), polytrimethylene terephthalate (PTT), and polyethylene naphthalate (PEN); polyamide fibers such as nylon; rayon fibers, and other synthetic fibers; hydrophilic nonwoven fabrics produced by mixing cotton, silk, hemp, pulp (cellulose) fibers, or the like, from the viewpoint of liquid permeability, flexibility and shape retaining ability upon formation into the above-mentioned water-absorbent sheet structure. Among these hydrophilic nonwoven fabrics, the hydrophilic nonwoven fabrics made of synthetic fibers are preferably used, from the viewpoint of increasing the shape retaining ability of the water-absorbent sheet structure or the like. Especially, hydrophilic nonwoven fabrics made of rayon fibers, polyolefin fibers, or polyester fibers are preferred. The hydrophilic nonwoven fabric made of synthetic fibers may contain a small amount of pulp fibers to an extent that would not increase the thickness of the water-absorbent sheet structure obtained. These hydrophilic nonwoven fabrics may be hydrophilic nonwoven fabrics made of single fibers mentioned above, or hydrophilic nonwoven fabrics made of two or more kinds of fibers in combination.

More specifically, spunbond nonwoven fabrics made of fibers selected from the group consisting of polyolefin fibers, polyester fibers and blends thereof are more preferred, from the viewpoint of increasing shape retaining ability of the water-absorbent sheet structure, and preventing pass of the water-absorbent resin through the nonwoven fabric. In addition, spunlace nonwoven fabrics made of rayon fibers as a main component are also more preferred as the nonwoven fabrics used in the present invention, from the viewpoint of even more increasing liquid absorbent properties and flexibility upon formation of the water-absorbent sheet structure. Among the spunbond nonwoven fabrics mentioned above, spunbond-meltblown-spunbond (SMS) nonwoven fabrics and spunbond-meltblown-meltblown-spunbond (SMMS) nonwoven fabrics, which have a multi-layered structure of polyolefin fibers are more preferably used, and especially the SMS nonwoven fabrics and the SMMS nonwoven fabrics each made of polypropylene fibers as a main component are preferably used. On the other hand, as the above-mentioned spunlace nonwoven fabrics, those of proper blends of main component rayon fibers with polyolefin fibers and/or polyester fibers are preferably used, and among them, rayon-PET nonwoven fabrics and rayon-PET-PE nonwoven fabrics are preferably used. The above-mentioned nonwoven fabrics may contain a small amount of pulp fibers to an extent that would not increase the thickness of the water-absorbent sheet structure.

The above-mentioned hydrophilic nonwoven fabric is preferably a hydrophilic nonwoven fabric having an appropriate bulkiness and a large basis weight, from the viewpoint of giving the water-absorbent sheet structure according to the present invention excellent liquid permeability, flexibility, shape retaining ability and cushioning property, and speeding up the liquid permeation rate of the water-absorbent sheet structure. The hydrophilic nonwoven fabric has a basis weight of preferably from 5 to 300 g/m$^2$, more preferably from 10 to 200 g/m$^2$, even more preferably from 11 to 100 g/m$^2$, and still even more preferably from 12 to 50 g/m$^2$. Also, the hydrophilic nonwoven fabric has a thickness of preferably in the range of from 200 to 1,500 μm, more preferably in the range of from 250 to 1,200 μm, and even more preferably in the range of from 300 to 1,000 μm.

In the water-absorbent sheet structure according to the present invention, it is preferable that the absorbent layer further contains an adhesive, from the viewpoint of increasing shape retaining ability of the water-absorbent sheet structure obtained. When the adhesive is used, the adhesive includes, for example, rubber-based adhesives such as natural rubbers, butyl rubbers, and polyisoprene; styrene-based elastomer adhesives such as styrene-isoprene block copolymers (SIS), styrene-butadiene block copolymers (SBS), styrene-isobutylene block copolymers (SIBS), and styrene-ethylene-butylene-styrene block copolymers (SEBS); ethylene-vinyl acetate copolymer (EVA) adhesives; ethylene-acrylic acid derivative copolymer-based adhesives such as ethylene-ethyl acrylate copolymer (EEA), and ethylene-butyl acrylate copolymer (EBA); ethylene-acrylic acid copolymer (EAA) adhesives; polyamide-based adhesives such as copolymer nylons and dimer acid-based polyamides; polyolefin-based adhesives such as polyethylenes, polypropylenes, atactic polypropylenes, and copolymeric polyolefins; polyester-based adhesives such as polyethylene terephthalate (PET), polybutylene terephthalate (PBT), and copolymeric polyesters; and acrylic-based adhesives. Among these adhesives, the ethylene-vinyl acetate copolymer adhesives, the styrene-based elastomer adhesives, the polyolefin-based adhesives, and the polyester-based adhesives are preferably used, from the viewpoint of high adhesive strength, thereby making it possible to prevent exfoliation of a hydrophilic nonwoven fabric and scattering of the water-absorbent resin in the water-absorbent sheet structure. These adhesives may be used alone, or they may be used in combination of two or more kinds.

The above-mentioned adhesive has a melting temperature or softening temperature of preferably from 50° to 180° C., and more preferably from 70° to 150° C., from the viewpoint of sufficiently fixing a water-absorbent resin to a hydrophilic nonwoven fabric, and at the same time preventing thermal deterioration or deformation of the hydrophilic nonwoven fabric.

The adhesive in the water-absorbent sheet structure according to the present invention is contained in an amount within the range of preferably from 0.05 to 2.0 times, more preferably in the range of from 0.08 to 1.5 times, and even more preferably in the range of from 0.1 to 1.0 time the amount of the water-absorbent resin contained (mass basis). It is preferable that the adhesive is contained in an amount of 0.05 times or more, from the viewpoint of having sufficient adhesion, thereby preventing exfoliation of the hydrophilic nonwoven fabrics themselves or scattering of the water-absorbent resin, and increasing shape retaining ability of a water-absorbent sheet structure. It is preferable that the adhesive is contained in an amount of 2.0 times or less, from the viewpoint of avoiding the inhibition of the swelling of the water-absorbent resin due to too strong adhesion to each other, thereby improving a liquid permeation rate or liquid leakage of a water-absorbent sheet structure.

In the water-absorbent sheet structure according to the present invention, the absorbent layer formed between the hydrophilic nonwoven fabrics contains at least a water-absorbent resin. For example, the water-absorbent sheet structure is formed by evenly dispersing a mixed powder of a water-absorbent resin and an adhesive over a hydrophilic nonwoven fabric, further overlaying a hydrophilic nonwoven fabric thereto, and subjecting the overlaid layers to heating, or optionally heating while pressing, at a temperature near a melting temperature of the adhesive. Alternatively, the water-absorbent sheet structure according to the present invention is formed by evenly dispersing a water-absorbent resin over an adhesive-coated hydrophilic nonwoven fabric, further overlaying an adhesive-coated hydrophilic nonwoven fabric thereto, and subjecting the overlaid layers to heating, optionally while pressing, or the water-absorbent sheet structure is also formed by sandwiching a water-absorbent resin between the hydrophilic nonwoven fabrics, and thereafter subjecting the overlaid layers to thermal embossing or the like.

The water-absorbent sheet structure according to the present invention can be produced by a method, for example, as described hereinbelow.

(a) A mixed powder of a water-absorbent resin and an adhesive is evenly dispersed over a hydrophilic nonwoven fabric, a hydrophilic nonwoven fabric is further overlaid thereto, and the overlaid layers are subjected to heating at a temperature near a melting temperature of the adhesive while pressing.

(b) A mixed powder of a water-absorbent resin and an adhesive is evenly dispersed over a hydrophilic nonwoven fabric, and passed through a heating furnace to fix the powder to an extent that the powder does not scatter. A hydrophilic nonwoven fabric is overlaid thereto, and the overlaid layers are subjected to heating while pressing.

(c) An adhesive is melt-coated over a hydrophilic nonwoven fabric, a water-absorbent resin is immediately thereafter evenly dispersed thereto to form a layer, further a hydrophilic nonwoven fabric melt-coated with the adhesive is overlaid from an upper side so that the coated side of the adhesive faces the side of the dispersed water-absorbent resin layer, the overlaid layers are subjected to pressing with a roller press or the like, optionally pressing while heating.

(d) A water-absorbent resin is evenly dispersed over a hydrophilic nonwoven fabric, a hydrophilic nonwoven fabric is further overlaid thereto, and the overlaid layers are subjected to thermal embossing, thereby heating the hydrophilic nonwoven fabrics themselves while pressing.

A water-absorbent sheet structure having a structure in which an absorbent layer containing a water-absorbent resin is sandwiched with two sheets of hydrophilic nonwoven fabrics from an upper side and a lower side can be obtained by producing a water-absorbent sheet structure, for example, according to the method shown in any one of these (a) to (d). Among these methods, the methods of (a), (c) and (d) are more preferred, from the viewpoint of convenience in the production method and high production efficiency. Here, the water-absorbent sheet structure can also be produced by combining the methods exemplified in (a) to (d). The number of sheets of the hydrophilic nonwoven fabrics is preferably two or more, and more preferably two.

In the present invention, the above-mentioned water-absorbent sheet structure can also take a structure in which a part or entire side of the absorbent layer thereof is fractionated into an upper side primary absorbent layer and a lower side secondary absorbent layer by using an appropriate breathable fractionating layer in a perpendicular direction (the thickness direction of the water-absorbent sheet structure). By having the above structure, the liquid absorbent properties of the water-absorbent sheet structure, especially slope liquid leakage, is dramatically improved.

The breathable fractionating layer has appropriate breathability and liquid-permeability, which may be a layer in which a particle-form substance such as a water-absorbent resin does not substantially pass therethrough. Specific examples thereof include reticular products such as nets having fine pores made of PE or PP fibers; porous films such as perforated films; sanitary papers such as tissue paper; and cellulose-containing synthetic fiber nonwoven fabrics such as air laid nonwoven fabrics made of pulp/PE/PP, or nonwoven fabrics made of synthetic fibers, such as rayon fibers, polyolefin fibers, and polyester fibers. Among them, the same nonwoven fabrics as those used in sandwiching the absorbent layer in the present invention are preferably used, from the viewpoint of the properties of the water-absorbent sheet structure obtained.

The water-absorbent resin in the secondary absorbent layer is used in an amount of preferably in the range of from 0.01 to 1.0 time, and more preferably in the range of from 0.1 to 1.0 time the amount of the water-absorbent resin used of the primary absorbent layer (mass ratio). The water-absorbent resin in the secondary absorbent layer is preferably 0.01 times or more, from the viewpoint of sufficiently exhibiting liquid absorbent properties of the secondary absorbent layer, and preventing liquid leakage, and the water-absorbent resin is preferably 1.0 time or less, from the viewpoint of increasing dry feel at the surface after the liquid absorption and reducing amount of re-wet.

The liquid absorbent properties of the water-absorbent sheet structure according to the present invention are influenced by the water-absorbent properties of the water-absorbent resin used. Therefore, it is preferable that the water-absorbent resin of the primary absorbent layer to be used in the present invention is those selected with favorable ranges in the water-absorbent properties, by taking the constitution of each component of the water-absorbent sheet structure or the like into consideration. In addition, the water-absorbent resin of the secondary absorbent layer may be identical to or different from the water-absorbent resin of the primary absorbent layer.

More specifically, an embodiment where a water-absorbent resin used in at least one of the absorbent layers is a water-absorbent resin obtained by reversed phase suspension polymerization method is preferred, an embodiment where a water-absorbent resin used in a secondary absorbent layer is a water-absorbent resin obtained by reversed phase suspension polymerization method is more preferred, and an embodiment where both the water-absorbent resins used in the primary absorbent layer and the secondary absorbent layer are water-absorbent resins obtained by reversed phase suspension polymerization method is even more preferred.

In addition, the water-absorbent sheet structure according to the present invention may properly be formulated with an additive such as a deodorant, an anti-bacterial agent, or a gel stabilizer.

In the water-absorbent sheet structure according to the present invention, at least one side of the upper side and the lower side of the above-mentioned water-absorbent sheet structure is subjected to embossing, and both the sides may be subjected to embossing.

The water-absorbent sheet structure according to the present invention is characterized in that a central region W1 of a water-absorbent sheet structure 1 along the structure is subjected to one wavy embossing extending along the longitudinal direction, wherein the embossing comprises one or more discontinued segments of the embossing. By providing one wavy embossing with a certain spacing as described above, the liquid is allowed to diffuse in the longitudinal direction. Also, "one" in (one) wavy embossing means that the number of the wavy embossing to which the water-absorbent sheet structure as shown in FIG. 1 is subjected in a width direction is one. Accordingly, although the wavy embossing having discontinued segments of embossing appears to be interpreted as plural embossing, in the present specification, such embossing is defined as one embossing regardless of the number of discontinued segments of embossing, so long as the wavy embossing in the width direction is one. Therefore, in a case of a wavy embossing as shown in, for example, FIG. 18, the number of the wavy embossing would be counted as two. Here, the number of the discontinued segments of embossing is not particularly limited because the number varies depending upon the length in the longitudinal direction of the water-absorbent sheet structure. It is preferable that the number of the discontinued segments is from 2 to 15 segments per water-absorbent sheet structure.

The above embossing is considered to play a role of a pathway for allowing a large amount of liquids to flow (liquid transport pathway); in a case where of continuous embossing without discontinued segments, there is nothing to hamper the liquid diffusion when the liquids are allowed to flow in a large amount, so that a liquid may diffuse before allowing it to be absorbed to a water-absorbent sheet structure, thereby making it likely to cause a liquid leakage from a longitudinal direction of the water-absorbent sheet structure. In addition, in a case where the embossing is not wavy but linear, the distance for a liquid transport pathway would be shortened, and in a case where plural wavy embossing are further provided in a width direction of the water-absorbent sheet structure, the number of the liquid transport pathways would increase, thereby similarly making it likely to cause a liquid leakage from a longitudinal direction of the water-absorbent sheet structure. The shape of the wavy embossing in the present specification, in other words the shape of the embossing between each of the tips of the wavy forms formed by wavy embossing, is not particularly limited, and the wavy embossing may be a straight line or a curve.

Next, embossing of a water-absorbent sheet structure of the present invention will be explained with reference to FIG. 1.

A central region W1 of a water-absorbent sheet structure 1 provided with wavy embossing 2 in the present invention, shown schematically in FIG. 1, has a width of preferably within the range of from 0.10 to 0.45 times, and more preferably from 0.15 to 0.40 times, based on an entire width of the water-absorbent sheet structure 1. The width is preferably 0.10 times or more, from the viewpoint of obtaining a region for diffusing a liquid and preventing a liquid leakage from a longitudinal direction of the water-absorbent sheet structure, and the width is preferably 0.45 times or less, from the viewpoint of enhancing diffusion of a liquid in a longitudinal direction of a liquid and improving a permeation rate of a liquid. When the width of the central region W1 becomes too large, the distance of a liquid transport pathway based on the width direction of a water-absorbent sheet structure becomes long, so that diffusion in a longitudinal direction is likely to be worsened, and that a permeation rate is also likely to be delayed.

The distance L1 between embossing provided in the water-absorbent sheet structure 1 is preferably within the range of from 1.0 to 4.0 cm, and more preferably within the range of from 1.5 to 3.0 cm. The distance is preferably 1.0 cm or more, from the viewpoint of appropriately hampering the diffusion of the liquids in the longitudinal direction, thereby preventing a liquid leakage from the longitudinal direction of the water-absorbent sheet structure, and the distance is preferably 4.0 cm or less, from the viewpoint of keeping the diffusion of the liquid in the longitudinal direction, and having a favorable permeation rate of the liquids. When the embossing contains plural discontinued segments, the distance between each of the embossing may be the same or different.

The water-absorbent sheet structure 1 according to the present invention is provided with linear embossing 4 in a direction from each of tips 3 of wavy forms formed by the wavy embossing 2, preferably each of tops 3 of the wavy forms, towards an edge portion contouring along the longitudinal direction of the water-absorbent sheet structure 1, thereby improving diffusion in a width direction of the water-absorbent sheet structure 1, and intersecting with a flow of a liquid moving in a longitudinal direction, thereby suppressing a liquid leakage in a longitudinal direction.

In the present invention, certain effects are exhibited by providing linear embossing 4 from each of tips 3 of wavy forms. In a case where embossing parts are overlapped, the surroundings of the overlapping parts form a region spatially closed as in a sac. Inside this closed region, when the absorbent resin of the absorbent layer absorbs a liquid and is allowed to swell, the absorbent resin would be in a state pressed onto upper and lower hydrophilic nonwoven fabrics, thereby hampering the swelling of the water-absorbent resin. As a result, in this closed region, it is more likely to cause the gel blocking phenomena of the water-absorbent resin, thereby making it likely to lower the absorbent abilities of the water-absorbent sheet structure such as slowing down the permeation rate. Therefore, it is preferable that linear embossing 4 from each of tops 3 of wavy forms is provided, from the viewpoint of minimizing the influence in the closed region mentioned above and suppressing the lowering of a permeation rate.

Here, the linear embossing is not necessarily provided in all the tips, and plural lines of linear embossing may be provided from one tip. The shape of the linear embossing in the present specification is not particularly limited, and the linear embossing may be a straight line or a curve. In the present specification, the tips of the wavy forms refer to parts of embossing including tops of wavy forms and vicinity thereof, for example, a part of embossing spreading in left and right centering about tops of wavy forms, the embossing part being within 0.3 times the wavelength of the wavy embossing.

One of the features of the present invention resides in that a branched structure of embossing formed by the wavy embossing 2 and the linear embossing 4 has an approximate Y-shaped form. In the tips of the wavy embossing, since embossing is overlapping in the branched structure as described above, the lowering of absorption properties of a water-absorbent sheet structure caused by a closed region formed in the surrounding of emboss overlapping parts can be avoided. As described above, since the embossing shape of the wavy emboss and the embossing shape of the linear emboss may be a straight line or a curve, the embossing constituting a branched structure in the above approximate Y-shaped form may be a linear embossing or curved embossing, or may be a mixture of the both.

The water-absorbent sheet structure 1 according to the present invention is provided with non-embossing regions W2, W2' that are not provided with embossing, extending along the longitudinal direction in the edge portion contouring along the longitudinal direction of the sheet structure, and in this region diffusion of a body liquid is lowered, thereby suppressing a liquid leakage in a width direction of the water-absorbent sheet structure.

Each of the non-embossing regions W2, W2' shown in FIG. 1 in the present invention has a width of preferably within the range of from 0.05 to 0.30 times, and more preferably within the range of from 0.08 to 0.25 times, that of the entire width of the water-absorbent sheet structure 1. The width is preferably 0.05 times or more, from the viewpoint of suppressing a liquid leakage from a water-absorbent sheet structure from a width direction, and the width is preferably 0.30 times or less, from the viewpoint of suppressing the lowering of a permeation rate as a water-absorbent sheet structure caused by undesirably having exceedingly enlarged region for lowering diffusion.

The area of the embossing provided on the water-absorbent sheet structure according to the present invention, i.e. an areal percentage, is within the range of from 2 to 25%, preferably within the range of from 3 to 20%, more preferably within the range of from 4 to 15%, and even more preferably within the range of from 4 to 8%, of the entire area of the side provided with embossing on the water-absorbent sheet structure. The area of the embossing is preferably 2% or more, from the viewpoint of accelerating the liquid diffusion from the embossing parts and speeding up a permeation rate of a liquid, and from the viewpoint of preventing deformation of the shape of the water-absorbent sheet structure due to the fixation of the water-absorbent resin to the water-absorbent sheet structure, and the area of the embossing is preferably 25% or less, from the viewpoint of preventing the liquid from being diffused which could possibly take place before allowing the liquid to be absorbed to the water-absorbent sheet structure, and preventing a liquid leakage from a water-absorbent sheet structure, from the viewpoint of not inhibiting the swelling of the water-absorbent resin, and from the viewpoint of softening a feel of the water-absorbent sheet structure obtained.

The term "the area of the embossing" as used herein refers to a value calculated from an area of a side contacting the water-absorbent sheet structure of a die for providing an embossing shape, of an apparatus used when subjected to embossing.

In the water-absorbent sheet structure according to the present invention, a method of subjecting the water-absorbent sheet structure to embossing includes a method using a pressure, heat, ultrasonic wave, an adhesive, or the like, and a method of a combination thereof may be also used. Here, when subjected to embossing, the sheet structure may be directly subjected to embossing upon pressing in the method mentioned above, or alternatively, a water-absorbent sheet structure before subjecting to embossing is once produced, and thereafter the sheet structure may be separately subjected to embossing. The embossing shape in the present invention is very unique as mentioned above, and an emboss having a desired shape can be provided by setting a die to provide an embossing shape, and the segments in which the embossing is discontinued can also be provided by appropriately setting a die.

The absorbent article according to the present invention can be obtained by sandwiching a water-absorbent sheet structure according to the present invention between a liquid-permeable sheet and a liquid-impermeable sheet. In a case where the side subjected to embossing is one side of the water-absorbent sheet structure, it is preferable that a liquid-permeable sheet is provided on the side subjected to embossing. As the liquid-permeable sheet and the liquid-impermeable sheet, known ones in the technical field of the present invention can be used, and as a method for sandwiching the structure sheet with these sheets, a known method can be employed.

EXAMPLES

The present invention will be specifically described hereinbelow by Examples and Comparative Examples, without intending to limit the scope of the present invention thereto.

The properties of the water-absorbent sheet structure were measured in accordance with the following methods.

<Evaluations of Liquid Permeation Rate Under Load and Amount of Re-Wet of Water-Absorbent Sheet Structure>

A water-absorbent sheet structure which was cut into rectangular strips having dimensions of 14 cm×30 cm in a manner that a longitudinal direction thereof is to be in a length direction (machine feeding direction) of the nonwoven fabric, was used as a sample.

In a 10 L container were placed 60 g of sodium chloride, 1.8 g of calcium chloride dihydrate, 3.6 g of magnesium chloride hexahydrate, and a proper amount of distilled water to completely dissolve. Next, 15 g of an aqueous 1% by mass poly(oxyethylene) isooctylphenyl ether solution was added thereto, and distilled water was further added to adjust the weight of the overall aqueous solution to 6,000 g. Thereafter, the mixed solution was colored with a small amount of Blue No. 1 to prepare a test solution.

A polyethylene air-through style porous liquid-permeable sheet having the same size as the sample (14 cm×30 cm) and a basis weight of 21 g/m$^2$ was placed over an upper side of a sample (water-absorbent sheet structure). In addition, a polyethylene liquid-impermeable sheet having the same size and basis weight as the sheet was placed on a lower side of the sample, to prepare a simple absorbent article. An acrylic plate of 10 cm×10 cm having a cylindrical cylinder with an inner diameter of 2.5 cm and of a height 17 cm at the central part was placed near the central section of this body liquid absorbent article, and further the weight was placed on the acrylic plate so as to apply a load of 2000 g in total to the sample. A 70 mL test solution was supplied thereto at one time. At the same time, a time period until the test solution was completely permeated into the body liquid absorbent article was measured with a stopwatch, which is referred to as a first permeation rate (seconds). Next, the same procedures were carried out 30 minutes thereafter and 60 minutes thereafter, to measure second and third permeation rates (seconds). A total of the number of seconds for the first to third permeation rates is referred to as a liquid permeation rate under load. After the termination of the measurements of each of the permeation rates, the presence or absence of a liquid leakage in a width direction of the water-absorbent sheet structure was visually confirmed.

After 120 minutes from the start of the feeding of the first test solution, the cylinder was removed, filter papers (about 80 sheets) of 10 cm each side, of which mass (Wa (g), about 70 g) was previously measured, were stacked near the liquid supplying position of the absorbent article, and a 5 kg weight of which bottom side has dimensions of 10 cm×10 cm was placed thereon. After 5 minutes of applying a load, the mass (Wb (g)) of the filter papers was measured, and an increased mass was defined as the amount of re-wet (g).

Amount of Re-wet($g$)=$Wb-Wa$

<Slope Leakage Test>

Figure 2:
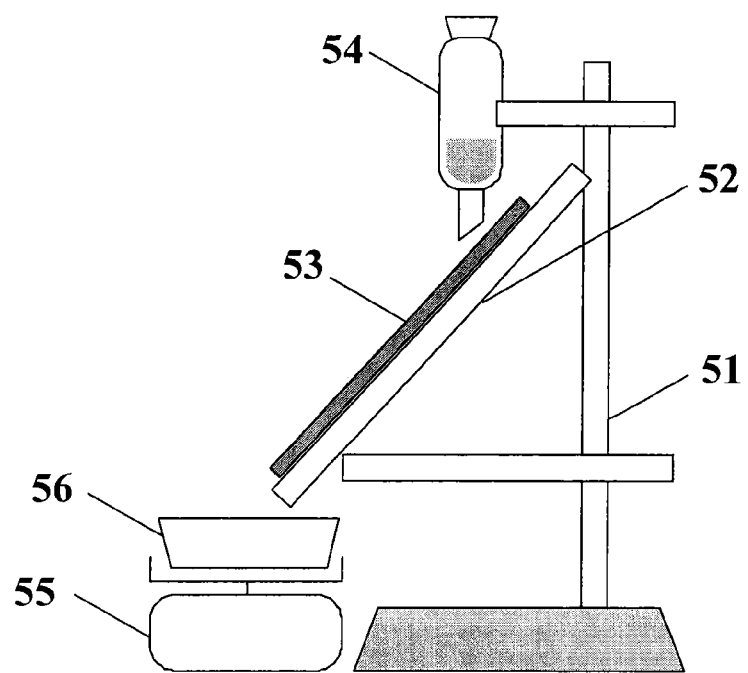
FIG. 2 The figure is a schematic view of an apparatus used for carrying out a slope leakage test.

A slope leakage test was conducted using an apparatus shown in FIG. 2.

Schematically, a mechanism is as follows. A commercially available stand 51 for experimental facilities was used to slope an acrylic plate 52 and fixed, the above-mentioned test solution was then supplied to an absorbent article 53 placed on the plate from a dropping funnel 54 positioned vertically above the absorbent article, and a leakage amount was measured with a balance 55. The detailed specifications are given hereinbelow.

An acrylic plate 52 had a length in the direction of the slope plane of 45 cm, and fixed so that an angle formed with a stand 51 against the horizontal is 45°±2°. The acrylic plate 52 had a width of 100 cm and a thickness of 1 cm, and plural absorbent articles 53 could be concurrently measured. The acrylic plate 52 had a smooth surface, so that a liquid was not detained or absorbed to the plate.

A dropping funnel 54 was fixed at a position vertically above the sloped acrylic plate 52 using the stand 51. The dropping funnel 54 had a volume of 100 mL, and an inner diameter of a tip end portion of about 4 mm, and an aperture of the cock was adjusted so that a liquid was supplied at a rate of 7 mL/s.

A balance 55 on which a tray 56 was placed was set at a lower side of the acrylic plate 52, and all the test solutions flowing down the plate were received as leakage, and the mass was recorded to the accuracy of 0.1 g.

A slope leakage test using an apparatus as described above was carried out in accordance with the following procedures. A water-absorbent sheet structure which was cut into a rectangular strip having dimensions of 14 cm×30 cm in a manner that the longitudinal direction is a length direction (machine feeding direction) of the hydrophilic nonwoven fabric was used as a sample. Next, an air-through style polyethylene liquid-permeable nonwoven fabric (basis weight: 21 g/m$^2$) of the same size was placed over an upper side of the sample, and further a polyethylene liquid-impermeable sheet having the same size and the same basis weight was placed on a lower side thereof to prepare a simple absorbent article 53. The simple absorbent article 53 was adhered on the acrylic plate 52 (in order not to stop leakage intentionally, the bottom end of the absorbent article 53 was not adhered to the acrylic plate 52).

Marking was put on the absorbent article 53 at a position 2 cm away in a downward direction from the center of a top end thereof, and a supplying inlet for the dropping funnel 54 was fixed so that the inlet was positioned at a distance 1 cm vertically above the marking.

A balance 55 was turned on, and tared so that the indication was zero, and thereafter 70 mL of the above-mentioned test solution was supplied at one time to the dropping funnel 54. An amount of liquid poured into a tray 56 after the test solution was allowed to flow over a sloped acrylic plate 52 without being absorbed into a water-absorbent sheet structure 53 was measured, and this amount of liquid was defined as a first leakage amount (g). The numerical value for this first leakage amount (g) was denoted as LW1.

Second and third test solutions were supplied in 10-minute intervals from the beginning of the first supply, and second and third leakage amounts (g) were measured, and the numerical values therefor were respectively denoted as LW2 and LW3.

Next, a leakage index was calculated in accordance with the following equation. The closer the approximation of the index to zero, the smaller the slope leakage amount of a water-absorbent sheet structure, especially an initial leakage amount, whereby it is judged to be an excellent water-absorbent sheet structure.

$$\text{Leakage Index:} L = LW1 \times 10 + LW2 \times 5 + LW3$$

<Measurement of Thickness of Water-Absorbent Sheet Structure>

A water-absorbent sheet structure which was cut into rectangular strips having dimensions of 14 cm×30 cm in a manner that a longitudinal direction thereof is to be in a length direction (machine feeding direction) of the nonwoven fabric, was used as a sample. The thickness of the resulting water-absorbent sheet structure was measured using a thickness measurement instrument (manufactured by Kabushiki Kaisha Ozaki Seisakusho, model number: J-B) at three measurement sites taken in a longitudinal direction, on the left end, the center, and the right end; for example, the left end was set at a site 3 cm away from the left side, the center was set at a site 15 cm away therefrom, and the right end was set at a site 27 cm away therefrom. As the width direction, a central part was measured. The measurement value for thickness was obtained by measuring three times at each site, and an average for each site was obtained. Further, the values at the left end, the center, and the right end were averaged, which was defined as a thickness of an overall water-absorbent sheet structure.

Example 1

A spunbond-meltblown-spunbond (hereinafter referred to as SMS) nonwoven fabric made of polypropylene having a width of 30 cm hydrophilically treated with a hydrophilic treatment agent (basis weight: 12 g/m$^2$, thickness: 150 µm, polypropylene content: 100%) as a hydrophilic nonwoven fabric was spread over a hot melt applicator (manufactured by HALLYS Corporation, Marshall 150) of which heating temperature was set at 150° C., and thereafter a styrene-butadiene-styrene copolymer (SBS, softening point: 85° C.) was coated as an adhesive over the nonwoven fabric at a basis weight of 10 g/m$^2$.

Next, a roller spreader (manufactured by HASHIMA CO., LTD., SINTERACE M/C) was charged at its supplying inlet with a crosslinked product of a partially neutralized sodium salt of acrylic acid polymer (manufactured by Sumitomo Seika Co., Ltd., AQUAKEEP SA55SX-II) as a water-absorbent resin. On the other hand, the above-mentioned hydrophilic nonwoven fabric coated with an adhesive was spread over a conveyor at the bottom side of the spreader. Subsequently, the spreading roller and the bottom side conveyor were operated, thereby allowing the crosslinked product of a partially neutralized sodium salt of acrylic acid polymer to evenly overlay over the above-mentioned hydrophilic nonwoven fabric coated with an adhesive at a basis weight of 120 g/m$^2$, to give an overlaid product.

The overlaid product obtained was sandwiched from an upper side with the above-mentioned SMS-hydrophilic nonwoven fabric to which the above-mentioned SBS was applied as an adhesive in the same manner as above at a basis weight of 10 g/m$^2$, and thereafter heat-fused with a thermal laminating machine (manufactured by HASHIMA CO., LTD., straight linear fusing press HP-600LF) of which heating temperature was set at 100° C. to integrate, to give an intermediate product of a water-absorbent sheet structure.

The intermediate product of a water-absorbent sheet structure obtained was spread over the hot melt applicator of which heating temperature was set at 150° C. in the same manner as described above, and thereafter the above-mentioned SBS was coated as an adhesive to the intermediate product of a water-absorbent sheet structure at a basis weight of 12 g/m$^2$.

Next, the roller spreader was charged at its supplying inlet with a crosslinked product of a partially neutralized sodium salt of acrylic acid polymer (manufactured by Sumitomo Seika Co., Ltd., AQUAKEEP 10SH-PB) as a water-absorbent resin. On the other hand, the above-mentioned intermediate product of a water-absorbent sheet structure coated with an adhesive was spread over a conveyor at the bottom side of the spreader. Subsequently, the spreading roller and the bottom side conveyor were operated, thereby allowing the above-mentioned crosslinked product of a partially neutralized sodium salt of acrylic acid polymer to evenly overlay over the intermediate product of a water-absorbent sheet structure coated with an adhesive at a basis weight of 120 g/m$^2$, to give an overlaid product.

The overlaid product obtained was sandwiched from an upper side with the above-mentioned SMS-nonwoven fabric to which the above-mentioned SBS was applied in the same manner as above as an adhesive at a basis weight of 12 g/m$^2$, and thereafter heat-fused with the above-mentioned thermal laminating machine of which heating temperature was set at 40° C. to integrate, to give a water-absorbent sheet structure before subjecting to embossing.

Figure 3:
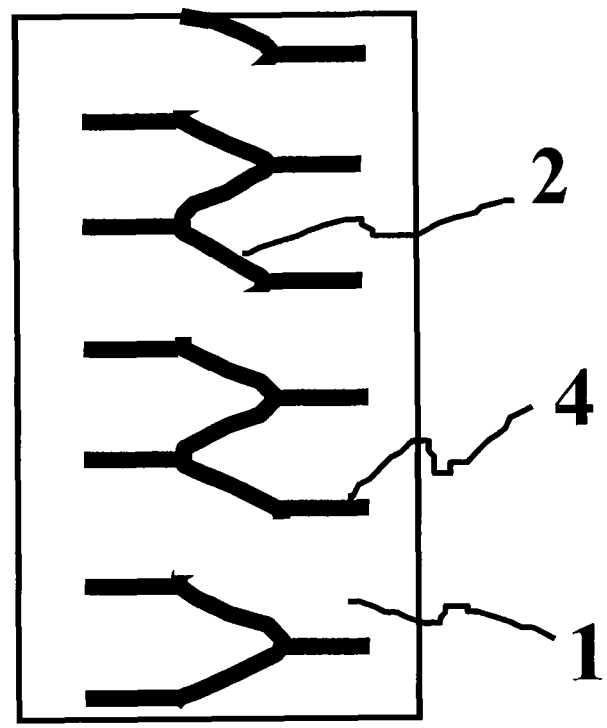
FIG. 3 The figure is a plan view of a water-absorbent sheet structure showing one example (Example 1) of the present invention.

The water-absorbent sheet structure before subjecting to embossing obtained was cut into rectangular strips having dimensions of 14 cm×30 cm in a manner that the longitudinal direction is a length direction (machine feeding direction) of the nonwoven fabric, and the above-mentioned water-absorbent sheet structure (one side) was subjected to embossing with a thermal embossing roller so as to have an embossing shape having the properties as listed in Table 1, and to form an embossing shape shown in FIG. 3, to give a water-absorbent sheet structure. Various measurements mentioned above were made for the water-absorbent sheet structures obtained. The results are shown in Table 2.

TABLE 1

Figure 4:
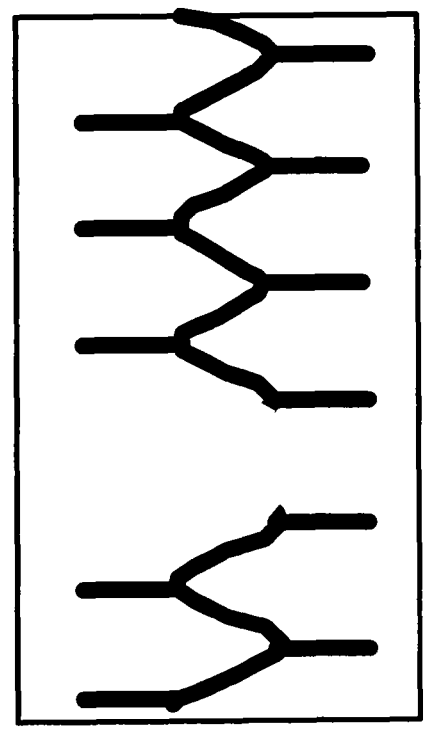
FIG. 4 The figure is a plan view of a water-absorbent sheet structure showing another example (Example 2) of the present invention.
Figure 5:
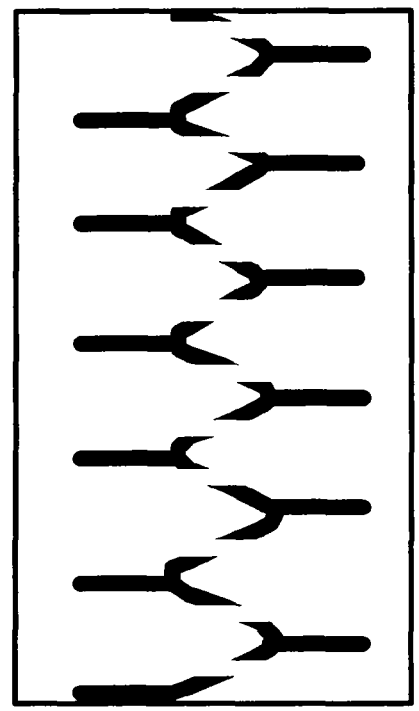
FIG. 5 The figure is a plan view of a water-absorbent sheet structure showing another example (Example 3) of the present invention.
Figure 6:
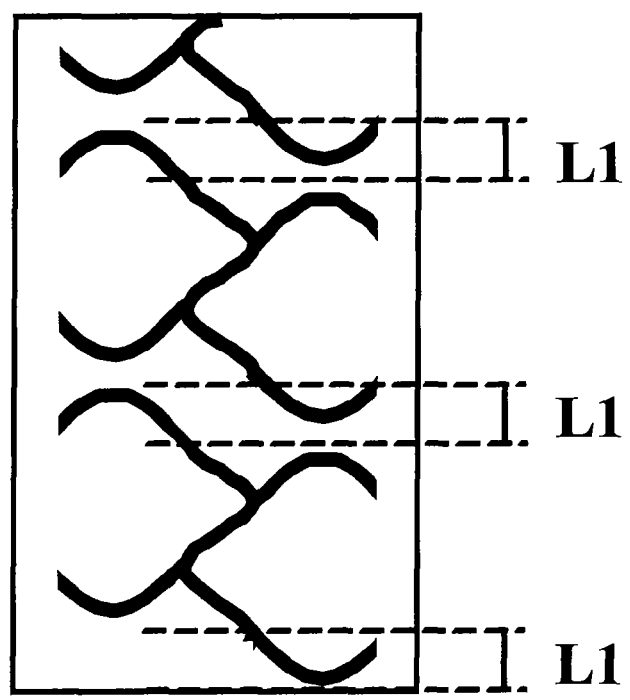
FIG. 6 The figure is a plan view of a water-absorbent sheet structure showing another example (Example 4) of the present invention.
Figure 7:
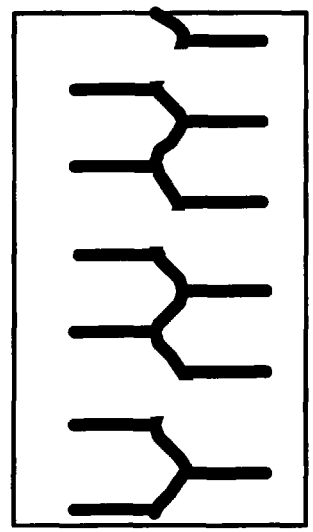
FIG. 7 The figure is a plan view of a water-absorbent sheet structure showing another example (Example 5) of the present invention.
Figure 8:
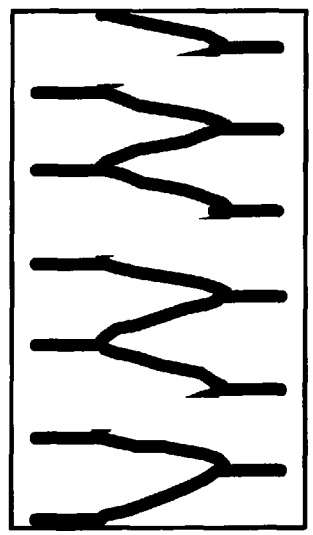
FIG. 8 The figure is a plan view of a water-absorbent sheet structure showing another example (Example 6) of the present invention.
Figure 9:
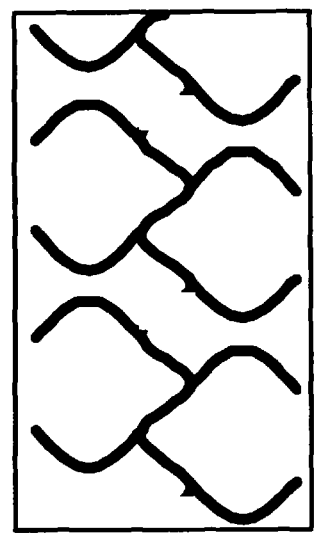
FIG. 9 The figure is a plan view of a water-absorbent sheet structure showing another example (Example 7) of the present invention.
Figure 10:
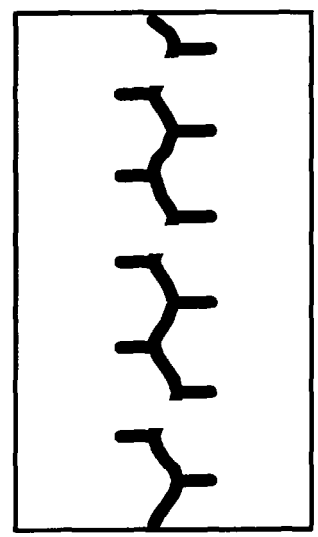
FIG. 10 The figure is a plan view of a water-absorbent sheet structure showing another example (Example 8) of the present invention.
Figure 11:
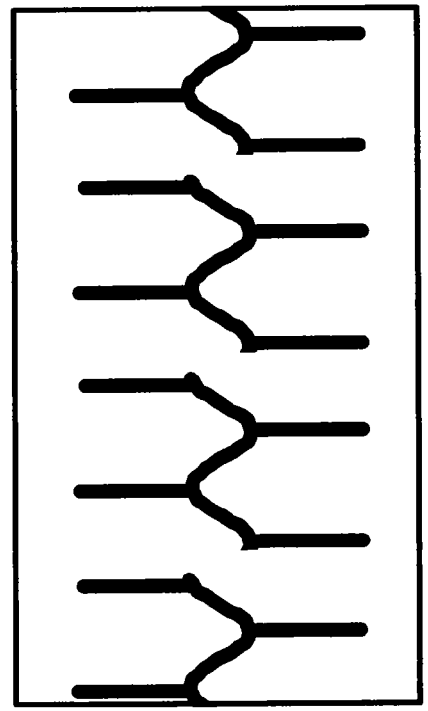
FIG. 11 The figure is a plan view of a water-absorbent sheet structure showing another example (Example 9) of the present invention.
Figure 12:
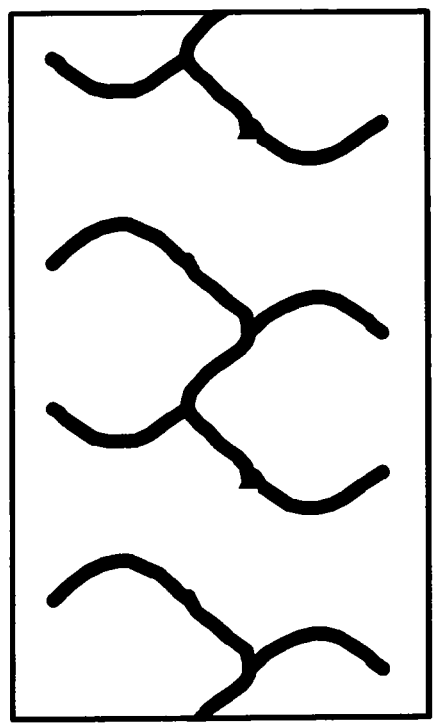
FIG. 12 The figure is a plan view of a water-absorbent sheet structure showing another example (Example 10) of the present invention.

| | Embossing Line Width [mm] | Central Region W1 [cm] | Central Region W1 Folds Based on Sheet Width | Non-Embossing Region W2 [cm] | Non-Embossing Region W2 Folds Based on Sheet Width | Non-Embossing Region W2' [cm] | Non-Embossing Region W2' Folds Based on Sheet Width | Distance Between Embossing L1 [cm] | Areal Percentage of Embossing [%] | Patterns of FIGS. |
|---|---|---|---|---|---|---|---|---|---|---|
| Ex. | | | | | | | | | | |
| 1 | 3 | 2.5 | 0.18 | 3.25 | 0.23 | 3.25 | 0.23 | 2.0 | 4 | FIG. 3 |
| 2 | 3 | 2.5 | 0.18 | 3.25 | 0.23 | 3.25 | 0.23 | 4.0 | 4 | FIG. 4 |
| 3 | 3 | 2.5 | 0.18 | 3.25 | 0.23 | 3.25 | 0.23 | 1.0 | 3 | FIG. 5 |
| 4 | 3 | 2.5 | 0.18 | 1.50 | 0.11 | 1.50 | 0.11 | 2.5 | 7 | FIG. 6 |
| 5 | 3 | 1.0 | 0.07 | 1.80 | 0.13 | 1.80 | 0.13 | 2.0 | 6 | FIG. 7 |
| 6 | 3 | 7.0 | 0.50 | 0.70 | 0.05 | 0.70 | 0.05 | 2.0 | 8 | FIG. 8 |
| 7 | 3 | 2.5 | 0.18 | 0.25 | 0.02 | 0.25 | 0.02 | 2.5 | 8 | FIG. 9 |
| 8 | 3 | 1.4 | 0.10 | 5.50 | 0.39 | 5.50 | 0.39 | 2.0 | 3 | FIG. 10 |
| 9 | 3 | 2.5 | 0.18 | 3.25 | 0.23 | 3.25 | 0.23 | 0.5 | 6 | FIG. 11 |
| 10 | 3 | 2.5 | 0.18 | 1.50 | 0.11 | 1.50 | 0.11 | 5.0 | 5 | FIG. 12 |
| Comp. Ex. | | | | | | | | | | |
| 1 | — | — | — | — | — | — | — | — | — | — |
| 2 | 1 | — | — | 0.00 | 0.00 | 0.00 | 0.00 | — | 10 | FIG. 13 |
| 3 | 3 | 2.5 | 0.18 | 3.25 | 0.23 | 3.25 | 0.23 | — | 5 | FIG. 14 |
| 4 | 3 | 4.2 | 0.30 | 4.90 | 0.35 | 4.90 | 0.35 | 2.5 | 4 | FIG. 15 |
| 5 | 2 | — | — | 2.10 | 0.15 | 2.10 | 0.15 | — | 8 | FIG. 16 |
| 6 | 3 | 0.3 | 0.02 | 1.50 | 0.11 | 1.50 | 0.11 | 2.0 | 4 | FIG. 17 |
| 7 | 3 | 4.2 | 0.30 | 1.80 | 0.13 | 1.80 | 0.13 | 2.5 | 8 | FIG. 18 |
| 8 | 1 | 2.5 | 0.18 | 3.25 | 0.23 | 3.25 | 0.23 | 2.0 | 1 | FIG. 19 |
| 9 | 6 | 2.5 | 0.18 | 1.50 | 0.11 | 1.50 | 0.11 | 1.2 | 28 | FIG. 20 |

Comparative Example 1

A water-absorbent sheet structure was obtained in the same manner as in Example 1 except that a water-absorbent sheet structure before subjecting to embossing was not provided with embossing work, and thereafter various kinds of properties were measured. The results are shown in Table 2.

Examples 2 to 10 and Comparative Examples 2 to 9

A water-absorbent sheet structure was obtained in the same manner as in Example 1 except that each of the sheet structures was provided with embossing shapes having the properties as shown in Table 1 and the shapes as shown in FIGS. 4 to 20, and thereafter various kinds of properties were measured. The results are shown in Table 2.

TABLE 2

| | Thickness [mm] | Permeation Rate Under Load [sec] 1 | Permeation Rate Under Load [sec] 2 | Permeation Rate Under Load [sec] 3 | Permeation Rate Under Load [sec] Total | Amount of Re-wet [g] | Liquid Leakage in Width Direction | Slope Leakage Test LW1 | Slope Leakage Test LW2 | Slope Leakage Test LW3 | Slope Leakage Test Index |
|---|---|---|---|---|---|---|---|---|---|---|---|
| Ex. | | | | | | | | | | | |
| 1 | 1.5 | 101 | 79 | 73 | 253 | 12.8 | Absence | 0.0 | 0.0 | 0.0 | 0 |
| 2 | 1.5 | 122 | 85 | 81 | 288 | 12.9 | Absence | 0.0 | 0.0 | 0.0 | 0 |
| 3 | 1.4 | 102 | 81 | 77 | 260 | 12.7 | Absence | 0.0 | 0.1 | 0.3 | 1 |
| 4 | 1.4 | 124 | 74 | 66 | 264 | 11.6 | Absence | 0.0 | 0.0 | 0.0 | 0 |
| 5 | 1.5 | 98 | 78 | 68 | 244 | 11.9 | Absence | 0.0 | 0.1 | 0.7 | 1 |
| 6 | 1.4 | 121 | 86 | 80 | 287 | 12.1 | Absence | 0.0 | 0.0 | 0.0 | 0 |

TABLE 2-continued

|   | Thickness [mm] | Permeation Rate Under Load [sec] | | | | Amount of Re-wet [g] | Liquid Leakage in Width Direction | Slope Leakage Test | | | |
|---|---|---|---|---|---|---|---|---|---|---|---|
|   |   | 1 | 2 | 3 | Total |   |   | LW1 | LW2 | LW3 | Index |
| 7 | 1.4 | 96 | 73 | 60 | 229 | 12.2 | Presence | 0.0 | 0.0 | 0.0 | 0 |
| 8 | 1.5 | 101 | 81 | 75 | 256 | 12.5 | Absence | 0.0 | 0.1 | 1.8 | 2 |
| 9 | 1.5 | 98 | 80 | 76 | 254 | 13.0 | Absence | 0.0 | 0.3 | 2.1 | 4 |
| 10 | 1.5 | 128 | 91 | 82 | 301 | 12.9 | Absence | 0.0 | 0.0 | 0.0 | 0 |
| Comp. Ex. | | | | | | | | | | | |
| 1 | 1.6 | 258 | 224 | 232 | 714 | 13.5 | Absence | 0.0 | 0.0 | 0.0 | 0 |
| 2 | 1.4 | 115 | 99 | 56 | 270 | 9.8 | Presence | 0.3 | 17.2 | 39.8 | 129 |
| 3 | 1.5 | 100 | 85 | 72 | 257 | 13.1 | Absence | 0.0 | 1.0 | 2.9 | 8 |
| 4 | 1.5 | 116 | 84 | 77 | 277 | 13.8 | Absence | 0.9 | 2.7 | 9.8 | 32 |
| 5 | 1.5 | 215 | 208 | 201 | 624 | 13.2 | Absence | 0.0 | 0.0 | 0.0 | 0 |
| 6 | 1.4 | 95 | 72 | 64 | 231 | 12.8 | Absence | 1.5 | 3.6 | 8.2 | 41 |
| 7 | 1.4 | 98 | 80 | 73 | 251 | 12.3 | Absence | 0.8 | 2.6 | 5.9 | 27 |
| 8 | 1.5 | 201 | 188 | 199 | 595 | 13.2 | Absence | 0.0 | 0.0 | 0.0 | 0 |
| 9 | 1.4 | 92 | 68 | 52 | 212 | 11.8 | Absence | 4.6 | 18.1 | 28.3 | 165 |

From the results shown in Table 2, the water-absorbent sheet structure of each example having a fast permeation rate, a small amount of re-wet, and favorable slope leakage was obtained.

Figure 13:
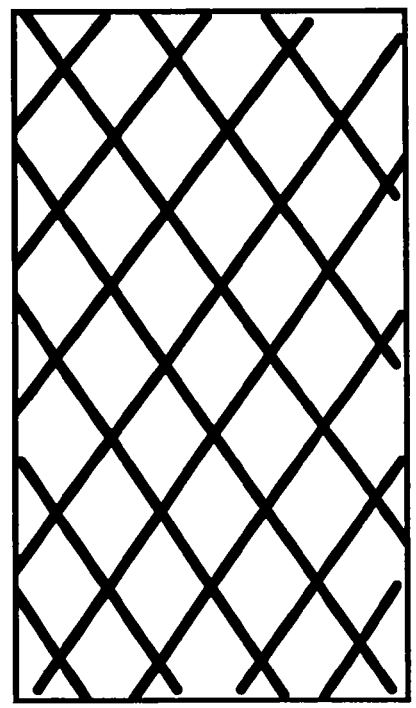
FIG. 13 The figure is a plan view of a water-absorbent sheet structure showing a comparative example (Comparative Example 2) of the present invention.
Figure 14:
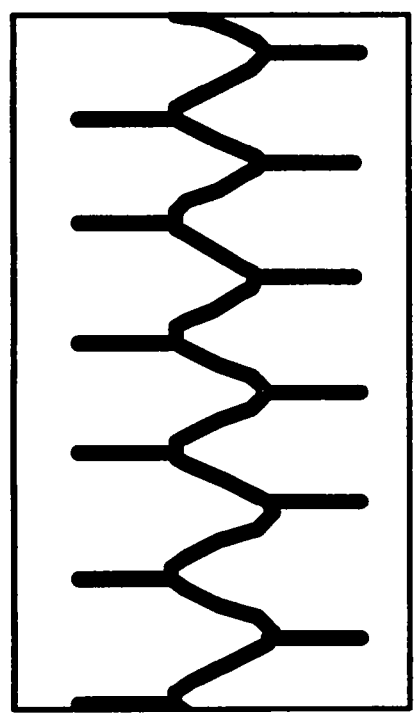
FIG. 14 The figure is a plan view of a water-absorbent sheet structure showing another comparative example (Comparative Example 3) of the present invention.
Figure 15:
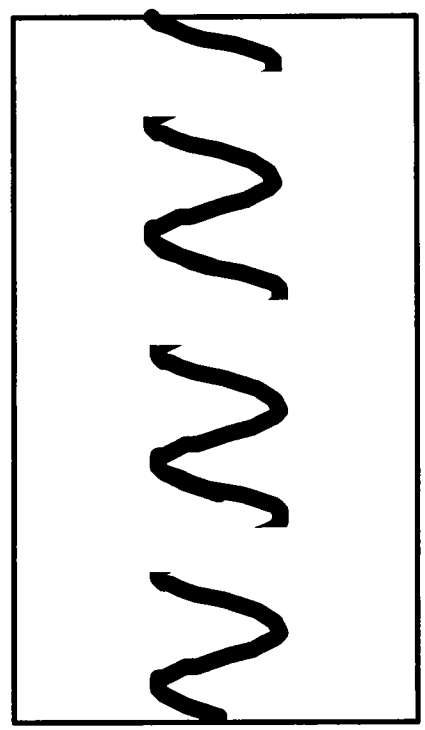
FIG. 15 The figure is a plan view of a water-absorbent sheet structure showing another comparative example (Comparative Example 4) of the present invention.
Figure 16:
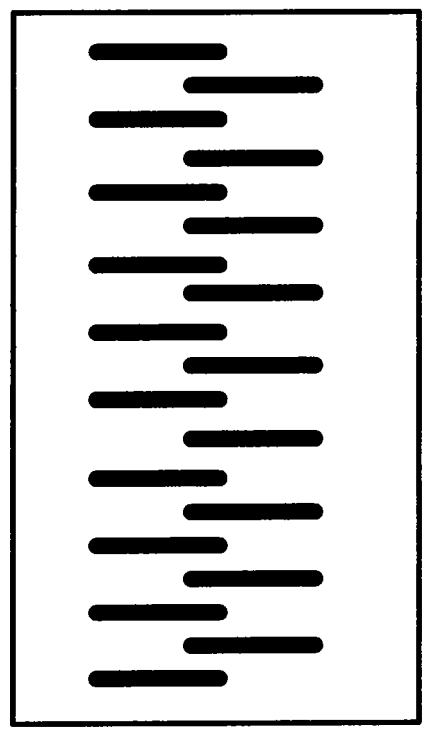
FIG. 16 The figure is a plan view of a water-absorbent sheet structure showing another comparative example (Comparative Example 5) of the present invention.
Figure 17:
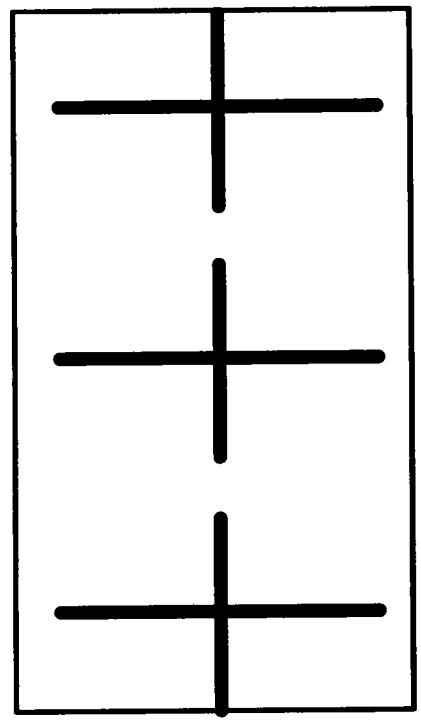
FIG. 17 The figure is a plan view of a water-absorbent sheet structure showing another comparative example (Comparative Example 6) of the present invention.
Figure 18:
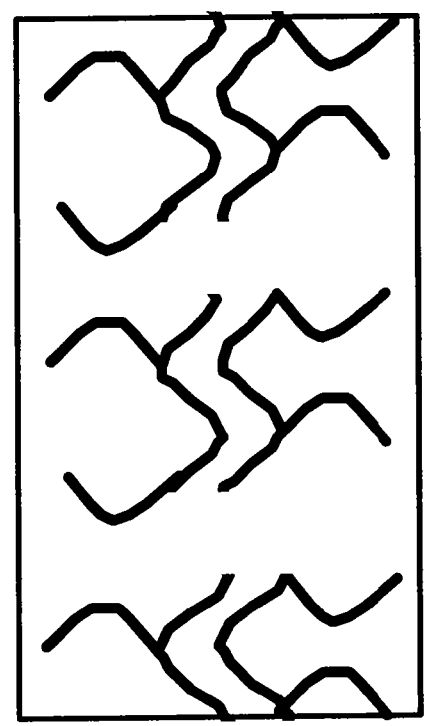
FIG. 18 The figure is a plan view of a water-absorbent sheet structure showing another comparative example (Comparative Example 7) of the present invention.
Figure 19:
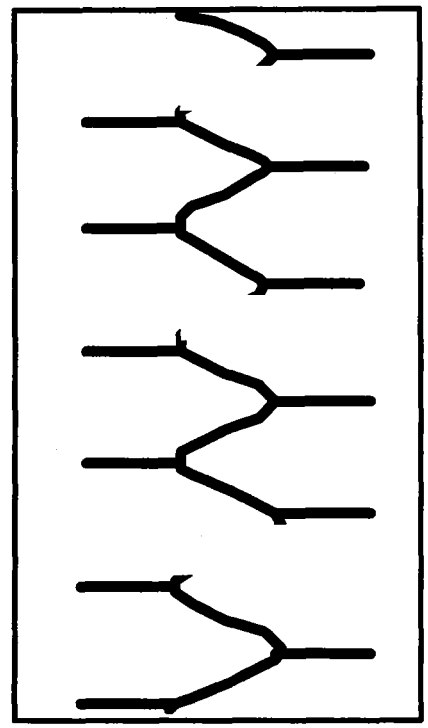
FIG. 19 The figure is a plan view of a water-absorbent sheet structure showing another comparative example (Comparative Example 8) of the present invention.
Figure 20:
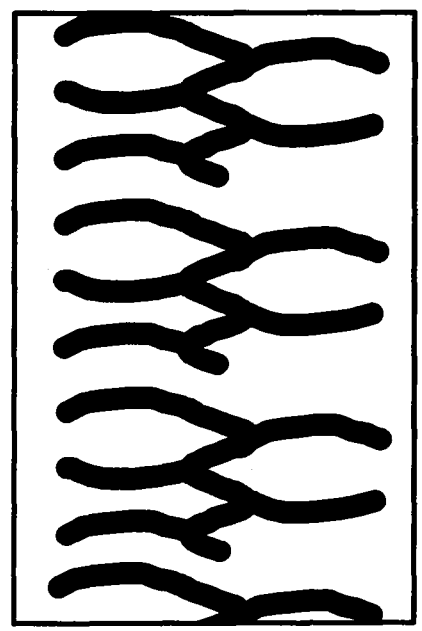
FIG. 20 The figure is a plan view of a water-absorbent sheet structure showing another comparative example (Comparative Example 9) of the present invention.

On the other hand, in Comparative Examples, all of a sheet structure not provided with embossing (Comparative Example 1), a sheet structure of which embossing shape is non-wavy (Comparative Example 2: FIG. 13; Comparative Example 5: FIG. 16; Comparative Example 6: FIG. 17), a sheet structure of which wavy embossing is continuous (Comparative Example 3: FIG. 14), a sheet structure not provided with linear embossment (Comparative Example 4: FIG. 15), a sheet structure provided with plural wavy embossing in a width direction of the water-absorbent sheet structure (Comparative Example 7: FIG. 18), a sheet structure of which embossing shape is similar to that of Example 1 but narrower in width of an embossing line, thereby having an areal percentage for embossment lower than a given range (Comparative Example 8: FIG. 19), and a sheet structure of which areal percentage for embossing exceeding a given range (Comparative Example 9: FIG. 20) could not simultaneously satisfy both the problems of improvement in permeation rates and prevention of leakage, thereby making it unsatisfactory as a water-absorbent sheet structure.

INDUSTRIAL APPLICABILITY

The water-absorbent sheet structure of the present invention has a fast permeation rate of a liquid and does not cause a liquid leakage, and can be suitably used in absorbent articles such as disposable diapers.

EXPLANATION OF NUMERICAL SYMBOLS 1 water-absorbent sheet structure
2 wavy embossing
3 tip
4 linear embossing
51 stand
52 acrylic plate
53 absorbent article
54 dropping funnel
55 balance
56 tray
L1 distance between embossing
W1 central region
W2 non-embossing region
W2' non-embossing region

The invention claimed is:

1. A water-absorbent sheet structure comprising a structure in which an absorbent layer comprising a water-absorbent resin is sandwiched with a hydrophilic nonwoven fabric from an upper side and a lower side of the absorbent layer, wherein at least one side of the upper side and the lower side of the water-absorbent sheet structure is subjected to embossing,
   wherein a central region of a water-absorbent sheet structure along a longitudinal direction of the structure is subjected to:
   wavy embossing comprising a wavy embossing extending along the longitudinal direction, and
   linear embossing in a direction from each of tips of wavy forms formed by the wavy embossing towards an edge portion contouring along the longitudinal direction of the water-absorbent sheet structure,
   wherein a branched structure of embossing formed by the wavy embossing and the linear embossing has an approximate Y-shape-form,
   wherein the edge portion contouring along the longitudinal direction of the water-absorbent sheet structure comprises non-embossing regions that are not subjected to embossing, extending along the longitudinal direction,
   wherein the brunched embossing comprises a plurality of segments each including the wavy embossing with the linear embossing, wherein the plurality of segments are discontinued along the longitudinal direction, and each of the plurality of segments extends continuously from one non-embossing region to the opposite non-embossing region of edge portion contouring along the longitudinal direction, and further
   wherein an area of the embossing provided on the water-absorbent sheet structure is from 2 to 25% of an entire area of the water-absorbent sheet structure.

2. The water-absorbent sheet structure according to claim 1, wherein the discontinued segments of the brunched embossing have a length, which is a distance between embossing, of from 1.0 to 4.0 cm.

3. The water-absorbent sheet structure according to claim 1, wherein the central region has a width of from 0.10 to 0.45 times an entire width of the water-absorbent sheet structure.

4. The water-absorbent sheet structure according to claim 1, wherein each of the non-embossing regions has a width of from 0.05 to 0.30 times the entire width of the water-absorbent sheet structure.

5. An absorbent article comprising the water-absorbent sheet structure according to 1, sandwiched between a liquid-permeable sheet and a liquid-impermeable sheet.

6. The water-absorbent sheet structure according to claim 2, wherein the central region has a width of from 0.10 to 0.45 times an entire width of the water-absorbent sheet structure.

7. The water-absorbent sheet structure according to claim 2, wherein each of the non-embossing regions has a width of from 0.05 to 0.30 times the entire width of the water-absorbent sheet structure.

8. The water-absorbent sheet structure according to claim 3, wherein each of the non-embossing regions has a width of from 0.05 to 0.30 times the entire width of the water-absorbent sheet structure.

9. An absorbent article comprising the water-absorbent sheet structure according to 2, sandwiched between a liquid-permeable sheet and a liquid-impermeable sheet.

10. An absorbent article comprising the water-absorbent sheet structure according to 3, sandwiched between a liquid-permeable sheet and a liquid-impermeable sheet.

11. An absorbent article comprising the water-absorbent sheet structure according to 4, sandwiched between a liquid-permeable sheet and a liquid-impermeable sheet.

\* \* \* \* \*